United States Patent
Coates

(10) Patent No.: US 10,137,267 B2
(45) Date of Patent: Nov. 27, 2018

(54) TRACHEOSTOMY TUBES

(71) Applicant: SMITHS MEDICAL INTERNATIONAL LIMITED, Kent (GB)

(72) Inventor: Daniel Jay Coates, Ogden Dunes, IN (US)

(73) Assignee: SMITHS MEDICAL INTERNATIONAL LIMITED, Kent (GB)

( * ) Notice: Subject to any disclaimer, the term of this patent is extended or adjusted under 35 U.S.C. 154(b) by 501 days.

(21) Appl. No.: 14/369,734

(22) PCT Filed: Jan. 4, 2013

(86) PCT No.: PCT/GB2013/000002
§ 371 (c)(1),
(2) Date: Jun. 30, 2014

(87) PCT Pub. No.: WO2013/110914
PCT Pub. Date: Aug. 1, 2013

(65) Prior Publication Data
US 2014/0360508 A1     Dec. 11, 2014

(30) Foreign Application Priority Data
Jan. 25, 2012 (GB) .................................. 1201315.7

(51) Int. Cl.
*A61M 16/04* (2006.01)
(52) U.S. Cl.
CPC .... *A61M 16/0465* (2013.01); *A61M 16/0425* (2014.02); *A61M 16/0427* (2014.02);
(Continued)

(58) Field of Classification Search
CPC .......... A61M 16/0434; A61M 16/0465; A61M 16/0497; A61M 16/044; A61M 16/0425;
(Continued)

(56) References Cited

U.S. PATENT DOCUMENTS

| 4,852,565 A * | 8/1989 | Eisele | ............... A61M 16/0465 |
| | | | 128/200.26 |
| 5,339,809 A | 8/1994 | Beck, Jr. et al. | |

(Continued)

FOREIGN PATENT DOCUMENTS

| CN | 101474448 A | 7/2009 |
| DE | 19745906 | 4/1999 |

(Continued)

OTHER PUBLICATIONS

PCT International Search Report and Written Opinion, ISA: EPO, relating to International Application No. PCT/GB2013/000002, dated Dec. 4, 2013 (Dec. 4, 2013).

*Primary Examiner* — Gregory Anderson
*Assistant Examiner* — Elliot S Ruddie
(74) *Attorney, Agent, or Firm* — Louis Woo

(57) ABSTRACT

A fenestrated tracheostomy tube has a shaft (1) made of a silicone or other soft material. The fenestrated region (10) located in the trachea (20) has two rows of several openings (11) along the center line of the tube. The openings (12) are formed in a separate plate (12) of a stiffer material bonded or moulded in an aperture (13) in the shaft (1) of the tube to give the shaft extra stiffness in this region.

10 Claims, 4 Drawing Sheets

(52) U.S. Cl.
CPC .... *A61M 16/0475* (2014.02); *A61M 16/0479* (2014.02); *A61M 16/044* (2013.01); *A61M 16/0434* (2013.01); *A61M 16/0497* (2013.01); *A61M 2205/02* (2013.01)

(58) Field of Classification Search
CPC .......... A61M 16/0427; A61M 16/0479; A61M 16/0475; A61M 2205/02; A61M 16/0443; A61M 16/0461; A61M 16/0468; A61M 16/0488; Y10S 128/911
USPC ............ 128/200.26, 207.12, 207.14, 207.15; 604/500; 623/9
See application file for complete search history.

(56) References Cited

U.S. PATENT DOCUMENTS

| | | | |
|---|---|---|---|
| 5,515,844 A * | 5/1996 | Christopher | A61M 16/10 128/200.26 |
| 5,957,978 A | 9/1999 | Blom | |
| 6,135,111 A * | 10/2000 | Mongeon | A61M 16/04 128/200.21 |
| 2006/0048775 A1 | 3/2006 | Dunlap | |
| 2009/0050157 A1 | 2/2009 | Bateman et al. | |
| 2009/0320853 A1 | 12/2009 | Kenowski et al. | |
| 2012/0180796 A1 * | 7/2012 | Bateman | A61M 16/0427 128/207.14 |

FOREIGN PATENT DOCUMENTS

| | | |
|---|---|---|
| JP | 63-124947 | 8/1988 |
| WO | WO 2005/094932 A1 | 10/2005 |

* cited by examiner

TRACHEOSTOMY TUBES

This invention relates to tracheostomy tubes of the kind having a shaft with a patient end, a machine end and a fenestrated region along its length including at least one opening at a location adapted to lie within the trachea.

Tracheostomy tubes are used to ventilate patients during and after surgery. As the patient begins to recover, it is preferable for him to be gradually weaned off breathing through the tube before it is completely removed. This can be done by partially deflating the cuff of the tube. Alternatively, a fenestrated tracheostomy tube can be used having one or more small openings in its side wall, so that a part of the patient's breathing passes through these openings and via his nose or mouth, instead of through the machine end of the tracheostomy tube. The fenestration openings can be closed by means of an inner cannula, which is removed when it is desired to allow gas to flow through the openings. The inner cannula could be replaced by an inner cannula with openings that align with the openings in the outer tube. Such fenestration openings also enable patients to talk since exhaled gas can be allowed to flow to the larynx via the openings. Examples of fenestrated tubes are described in GB1522632, U.S. Pat. Nos. 4,852,565, 5,771,888, 6,722,367, 5,957,978 and 7,987,851. Such fenestrated tubes can be provided satisfactorily but, where the tube is of a soft material, such as silicone, the removal of the material from the wall of the shaft to create the fenestrations can weaken the tube in the fenestrated region to the extent that the tube can be prone to buckling and collapse in this region.

It is an object of the present invention to provide an improved tracheostomy tube.

According to one aspect of the present invention there is provided a tracheostomy tube of the above-specified kind, characterised in that the shaft is formed of a relatively soft material and that the fenestrated region includes means for stiffening the fenestrated region.

The fenestrated region preferably includes two rows of a plurality of openings on opposite sides of a centre line of the shaft. The shaft may be of a silicone material. The means for stiffening the fenestrated region may include a plate of material stiffer than the material of the shaft, the or each opening being formed in the plate. The plate preferably provides the inner and outer surfaces of the fenestrated region. Alternatively, the or each opening may be formed through the material of the shaft, the fenestrated region including a strip of material extending along only the fenestrated region. The strip is preferably bonded in a channel extending longitudinally along the fenestrated region.

According to another aspect of the present invention there is provided a tracheostomy tube having a shaft of a first material with a patient end, a machine end and a fenestrated region along its length, characterised in that the fenestrated region includes a plate of a second material stiffer than the first material, and that the plate includes at least one opening therethrough such that gas can flow from the tube via the opening.

According to a further aspect of the present invention there is provided a tracheostomy tube having a shaft of a first material with a patient end, a machine end and a fenestrated region along its length including a plurality of openings from the tube, characterised in that the fenestrated region includes a strip of a second material stiffer than the first material extending longitudinally along the region between the openings.

The shaft of the tube may be of a silicone material.

A tracheostomy tube according to the present invention will now be described, by way of example, with reference to the accompanying drawings, in which.

Figure 1:
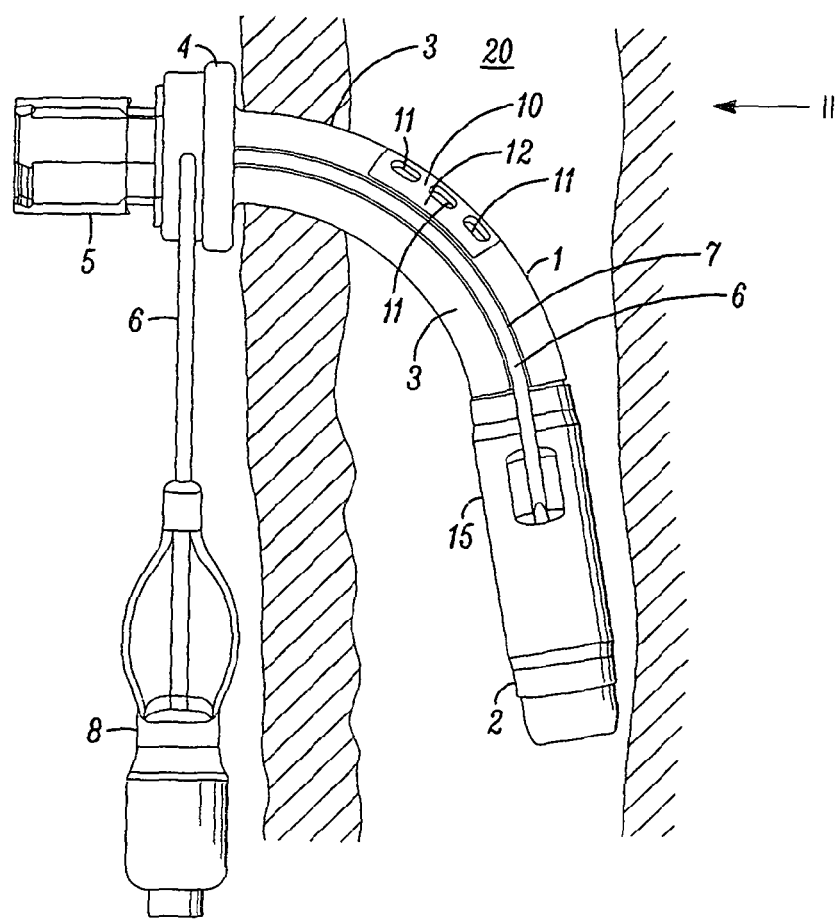
FIG. 1 is a side elevation view of the tube illustrating its position in the trachea.
Figure 2:
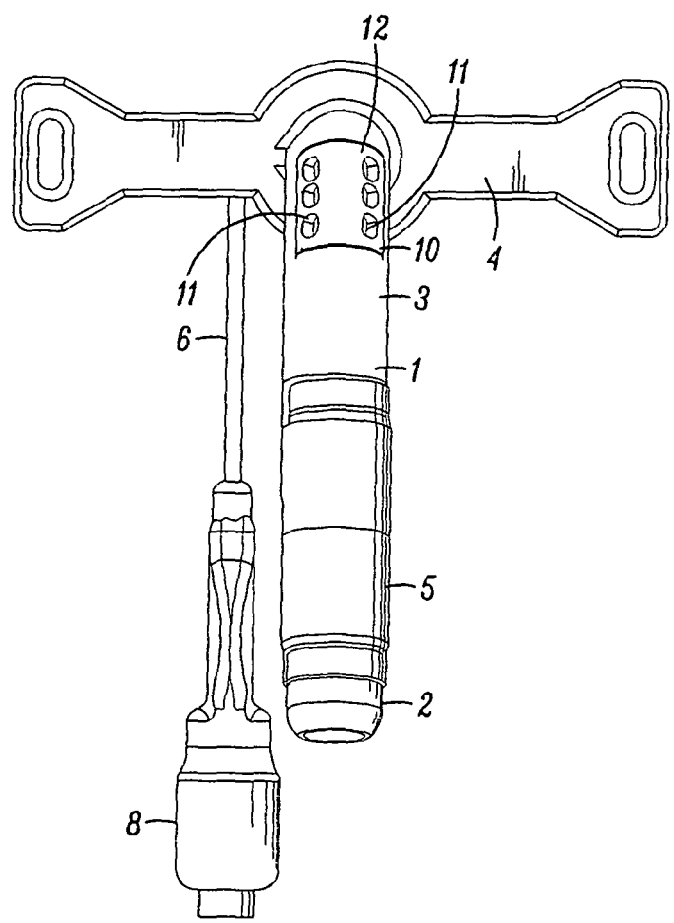
FIG. 2 is a view of the tube along the arrow II in FIG. 1.

With reference first to FIGS. 1 to 4, the tracheostomy tube comprises a moulded shaft 1 of a soft, flexible first material, typically silicone, and having a circular cross-section. The patient end region 2 of the tube is straight and communicates with a curved intermediate region 3, which extends to a neck flange 4 and a conventional machine end coupling 5. A sealing member in the form of an inflatable cuff 15 (shown deflated) encircles the patient end region 2, the interior of the cuff communicating with an inflation line 6 extending along a groove 7 formed along one side of the shaft 1. The inflation line 6 extends through the neck flange 4 and is terminated at its machine end by a connector and inflation indicator 8. As so far described, the tube is conventional.

The tube shaft 1 includes a fenestrated region 10 formed substantially midway along the curved region 3 at a location where it lies centrally of the trachea airway 20 during use. The fenestrated region 10 has six openings or holes 11 through the wall of the shaft 1 arranged in two rows of three holes each extending longitudinally side-by-side on opposite sides of the centre line of the shaft. Spacing the holes 11 away from the centre line of the shaft in this way reduces the risk that a suction catheter, endoscope or the like inserted in the tube will snag on the holes. It also reduces the risk that a small diameter catheter or instrument inserted in the tube could inadvertently pass through a fenestration hole and possibly cause trauma to the patient. Typically, the holes 11 are elongated with rounded ends being about 4 mm long and about 2 mm wide although the size and number of holes will vary according to the size of the tube. The total area of the holes 11 is preferably about 10% greater than the cross-sectional area of the interior of the shaft 1. The holes 11 are located on the external or convex, outer side of the curved region 3 so that, in use, they face upwards along the trachea 20, that is, towards the larynx.

Figure 3:
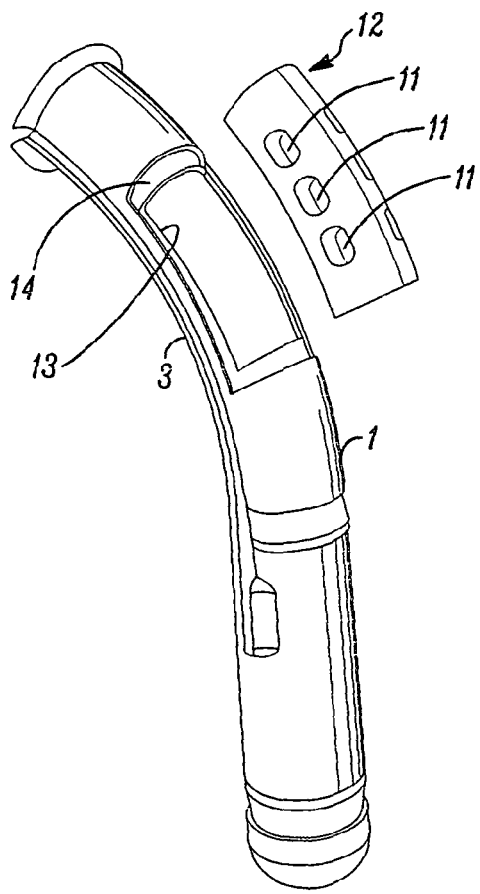
FIG. 3 is a perspective view of a part of the tube with the fenestrated plate separated.
Figure 4:
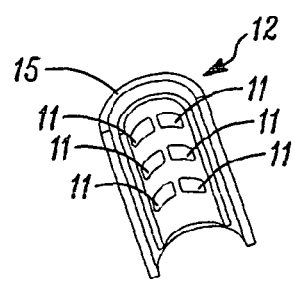
FIG. 4 is a perspective view of the inner side of the fenestrated plate.

The tube differs from conventional fenestrated tubes in that the fenestration holes 11 are not formed through the material of the tube shaft 1 itself but in a separate plate 12 as shown most clearly in FIGS. 3 and 4. The plate 12 is rectangular and is curved across its width and along its length to the same curvature as that of the shaft 1. Typically, the width of the plate 12 is such that it extends around about half the circumference of the shaft 1 and its length is such that it extends along about half the length of the curved region 3, being located about midway along the curved region. The plate 12 is formed of a second material stiffer than the material of the main body of the shaft 1, such as by moulding of a thermoplastic or thermosetting plastics material. The plate need not be formed of a plastics material but could, for example, be of a non-ferrous metal.

FIG. 3 shows an arrangement where the plate 12 is fitted with the shaft 1 after the shaft has been moulded, the plate sitting in an aperture provided by a rectangular recess 13 formed in the shaft and resting on a ledge 14 around the inside of the recess. FIG. 4 shows that the plate 12 has step 15 around its periphery on its inner side so that, when fitted in the recess 13, both the inner and outer surfaces of the plate form a smooth, stepless continuation of the internal and external surfaces of the shaft 1. The plate 12 thereby provides the inner and outer surfaces of the fenestrated region 10. The plate 12 could be secured in the recess 13 by means of an adhesive. Alternatively, the plate 12 could be attached with or embedded in the shaft during formation of the shaft, such as being overmoulded by the shaft material. The tube could be used with a conventional inner cannula (not shown) in the usual way to block the fenestration holes 11 when it is necessary for all gas to be restricted to flow along the length of the tube.

The stiffer nature of the plate 12 increases the overall stiffness of the shaft 1 in the fenestrated region 10 sufficiently to ensure that the tube does not buckle or kink in this region during normal use. The present invention enables the advantages of silicone tubes, that is, their flexibility and softness, to be retained in a tube having a fenestrated region. This is a particular advantage because it enables patients using these more comfortable and atraumatic tubes to be given some speech function or to be weaned off mechanical ventilation.

Figure 5:
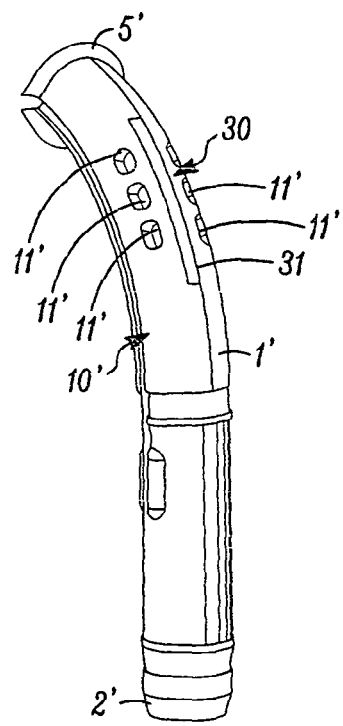
FIG. 5 is a perspective view of a part of an alternative tube with a strengthening strip.
Figure 6:
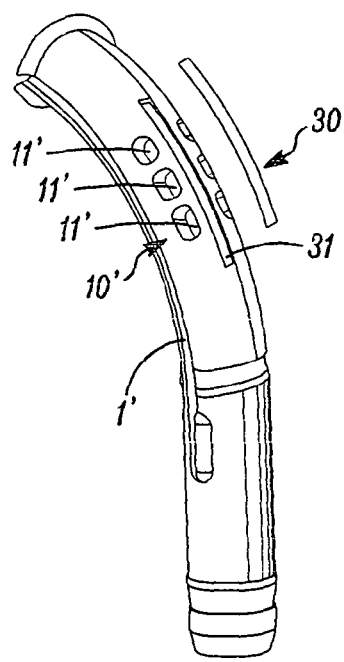
FIG. 6 shows the part of FIG. 5 with the strengthening separated from the tube.

The fenestrated region could be stiffened in other ways, apart from by means of the stiffening plate 12 through which the fenestrations 11 are formed. FIGS. 5 and 6 show an alternative tube where components similar to those in FIGS. 1 to 4 are given the same reference numerals with the addition of a prime '. In this alternative tube the shaft 1' is similarly of a first relatively soft, flexible material, such as silicone, but the fenestration openings 11' are formed through the shaft material itself. The fenestrated region 10' is stiffened instead by means of a strip 30 of second, stiff material such as a thermoplastic, a thermosetting plastic or a non-ferrous metal preformed to the curvature of the fenestrated region. The strip 30 is about 1 mm wide, about 0.5 mm thick and about 6 mm long but, it will be appreciated that its dimensions will vary according to the gauge of the tube. The strip 30 is bonded with the shaft 1' in a channel 31 extending longitudinally along the outside of the shaft between the two rows of fenestration openings 11' on the outside of the curve of the shaft. The channel 31 is moulded in the shaft with the same profile as the strip 30 so that the strip fits snugly in the channel and the tube has a smooth external surface. Alternatively, the strip could be embedded within the thickness of the shaft by overmoulding during formation of the shaft.

The invention claimed is:

1. A tracheostomy tube having a shaft with a length, a patient end, a machine end and a fenestrated region locating substantially midway along the length and spaced from the machine end and the patient end including at least one opening at a location adapted to lie within the trachea, characterized in that the shaft is formed of a first material that is relatively soft and that the fenestrated region of the tube is formed only by a plate that includes the at least one opening, the plate formed of a second material that is stiffer than the first material to increase the overall stiffness of the shaft at the fenestrated region such that the portion of the shaft between the patient end of the tube and the patient end of the plate is more flexible than the fenestrated portion.

2. A tracheostomy tube according to claim 1, characterized in that the fenestrated region includes two rows of a plurality of openings on opposite sides of a center line of the shaft.

3. A tracheostomy tube according to claim 1, characterized in that the shaft is of a silicone material.

4. A tracheostomy tube according to claim 1, characterized in that the plate provides the inner and outer surfaces of the fenestrated region.

5. A tracheostomy tube having a shaft with a length, a patient end, a machine end and a fenestrated region locating substantially midway along the length and spaced from the machine end and the patient end, the shaft formed of a first material that is relatively soft, wherein the fenestrated region is fitted only with a plate having at least one opening formed of a second material that is stiffer than the first material so that the overall stiffness of the shaft at the fenestrated region is increased such that the portion of the shaft between the patient end of the tube and the patient end of the plate is more flexible than the fenestrated portion.

6. A tracheostomy tube of claim 5, wherein the plate forms a smooth, stepless continuation of the internal and external surfaces of the shaft.

7. A tracheostomy tube of claim 5, wherein the plate is fitted to a recess formed at the fenestration region of the shaft to provide the inner and outer surfaces of the fenestration region.

8. A tracheostomy tube of claim 5, wherein the overall stiffness of the shaft at the fenestration region is increased sufficiently to ensure that the tube does not buckle or kink at the fenestration region during normal use.

9. A tracheostomy tube of claim 5, wherein there are multiple openings at the plate.

10. A tracheostomy tube having a shaft with a length, a patient end, a machine end and a fenestrated region locating substantially midway along the length and spaced from the machine end and the patient end including at least one opening at a location adapted to lie within the trachea, characterized in that the shaft is formed of a first material that is relatively soft and that the tube includes a plate formed of a second material that is stiffer than the first material at the fenestrated region to increase the stiffness of the shaft at the fenestrated region relative to the patient end, the plate forming the external surface of the shaft at the fenestrated region, and that the plate includes the at least one opening.

* * * * *